US006509514B1

(12) United States Patent
Kneteman et al.

(10) Patent No.: US 6,509,514 B1
(45) Date of Patent: Jan. 21, 2003

(54) CHIMERIC ANIMAL MODEL SUSCEPTIBLE TO HUMAN HEPATITIS C VIRUS INFECTION

(75) Inventors: Norman M. Kneteman, Edmonton (CA); D. Lorne Tyrrell, Edmonton (CA); David F. Mercer, Edmonton (CA)

(73) Assignee: KMT Hepatech, Inc., Edmonton (CA)

( * ) Notice: Subject to any disclaimer, the term of this patent is extended or adjusted under 35 U.S.C. 154(b) by 0 days.

(21) Appl. No.: 09/528,120

(22) Filed: Mar. 17, 2000

(51) Int. Cl.$^7$ .................... A01K 67/027; G01N 33/00; C12N 15/00
(52) U.S. Cl. .................. 800/3; 800/18; 800/21; 800/25
(58) Field of Search ............................ 800/8, 9, 18, 3, 800/21, 25

(56) References Cited

U.S. PATENT DOCUMENTS

| | | | |
|---|---|---|---|
| 5,652,373 A | 7/1997 | Reisner | 800/11 |
| 5,709,843 A | 1/1998 | Reisner | 424/9.2 |
| 5,804,160 A | 9/1998 | Reisner | 424/9.1 |
| 5,849,288 A | 12/1998 | Reisner | 424/93.21 |
| 5,849,987 A | 12/1998 | Reisner | 800/11 |
| 5,858,328 A | 1/1999 | Reisner | 424/9.2 |
| 5,866,757 A | 2/1999 | Reisner | 800/11 |
| 5,980,886 A * | 11/1999 | Kay et al. | 424/93.21 |
| 5,994,617 A * | 11/1999 | Dick et al. | 800/8 |
| 6,034,297 A * | 3/2000 | Vierling | 800/9 |

FOREIGN PATENT DOCUMENTS

| | | |
|---|---|---|
| EP | 0 438 053 | 7/1991 |
| WO | WO 93 07165 | 4/1993 |
| WO | WO 94 02601 | 2/1994 |
| WO | WO 94 27556 | 12/1994 |
| WO | WO 96 18419 | 6/1996 |
| WO | WO 98 42824 | 10/1998 |
| WO | WO 99/16307 | 4/1999 |
| WO | WO 99 46598 | 9/1999 |
| WO | WO 00/17338 | 3/2000 |
| WO | WO 01 32009 | 5/2001 |

OTHER PUBLICATIONS

M Houghton, Fields Virology, "Hepatitis C Viruses," 1996, 3rd Ed., Chap. 32, pp. 1035–1036.*
CA Kappel et al., Current Biology, "Regulating gene expression in transgenic animals," 1992, 3: 548–553.*
LJ Mullins et al., Transgenesis in Nnmurine Species, "Perspectives Series:Molecular Medicine in Genetically Engineered Animals," Supp.1996, vol. 98, No. 11, pp. S37–S40.*
RJ Wall, Theriogenology, "Transgenic Livestock: Progress and Prospects for the Future," 1996, 45:57–68.*
L–M Houdebine, Journal of Biotechnology, "Production of pharmaceutical proteins from transgenic animals," 1994, 34:269–287.*

Toth, L.R. et al. (1996) "Two Distinct apolipoprotein B alleles in mice generated by a single 'in–out' targeting", *Gene: An International Journal on Genes and Genomes*, G.B.,Elsevier Science, Publishers, Barking, vol. 178 (1):161–168.
Weglarz et al. (2000) "Hepatocyte Transplantation into Diseased Mouse Liver", *American Journal of Pathology*, vol. 157(6):1963–1974.
Vrancken–Peeters et al. (1997) "Expansion of Donor Hepatocytes After Recombinant Adenovirus–Induced Liver Regeneration in Mice" Hepatology, vol. 25(4): 884–888.
McBurney et al. (1994) "Murine PGK–1 Promoter Drives Widespread But Not Uniform Expression in Transgenic Mice" Developmental Dynamics, vol. 200(4): 278–298.
Lieber et al. (1995) "Adenovirus–mediated Urokinase Gene Transfer Induces Liver Regeneration and Allows for Efficient Retrovirus Transduction of Hepatocytes in vivo" Proc. National Academy of Science, Genetics, vol. 92(20): 6210–6214.
Lieber et al. (1995) "A Modified Urokinase Plasminogen Activator Induces Liver Regeneration Without Bleeding" Human Gene Therapy, vol. 6: 1029–1037.
Mercer et al. (2001) "Hepatitis C Virus replication in Mice With Chimeric Human Livers" Nature Medicine, vol. 7(8): 1–7.
Nelson Fausto (2001) "A Mouse Model For Hepatitis C Virus Infection?" Nature Medicine, vol. 7(8) 890–891.
Dandri et al. (2001) "Repopulation of Mouse Liver With Human Hepatocytes and In Vivo Infection With Hepatitis B Virus" Hepatology, 33(4) 981–988.
Crabb (2001) "Hard–Won Advances Spark Excitement About Hepatitis C" Science, vol. 294: 506–507.
Jean–Pierre Bronowicki, et al. "Hepatitis C Virus Persistence in Human Hematopoietic Cells Injected Into SCID Mice" Hepatology 28:211–8 (1998).
A.P. Dhillon, et al., "Pathology of Hepatitis C Virus Infection", Histopathology 26:297–309 (1995).
Chantal Fournier, et al, *In Vitro Infection of Adult Normal Human Hepatocytes in Primary Culture by Hepatitis C Virus*, J. Gen. Virol. 79,(Pt 10); 2367–2374 (1998).

(List continued on next page.)

*Primary Examiner*—Scott D. Priebe
*Assistant Examiner*—Peter Paras, Jr.
(74) *Attorney, Agent, or Firm*—Bozicevic, Field & Francis LLP; Carol L. Francis (57) ABSTRACT

The present invention features a non-human animal model that is susceptible to infection by human hepatotrophic pathogens, particularly human hepatitis C virus (HCV). The model is based on a non-human, immunocompromised xenogeneic transgenic animal having a human-mouse chimeric liver, where the transgene provides for expression of a urokinase-type plasminogen activator in the liver. The invention also features methods for identifying candidate therapeutic agents, e.g., agents having antiviral activity against HCV infection.

18 Claims, 4 Drawing Sheets

OTHER PUBLICATIONS

Eithan Galun, et al., "Hepatitis C Virus Viremia in SCID→BNX Mouse Chimera", J Infect Dis. 172:25–30 (1995).

Janice L. Heckel, et al., "Neonatal Bleeding In Transgenic Mice Expressing Urokinase–Type Plasminogen Activator", Cell 62:447–456 (1990).

T. Ito, et al., "Cultivation of Hepatitis C Virus in Primary Hepatocyte Culture from Patients with Chronic Hepatitis C Results in Release of High Titre Infectious Virus", J. Gen Virol. 77:1043 (1995).

Pietro Lampertico, et al., "Development and Application of an In Vitro Model for Screening Anit–hepatitis B Virus Therapeutics", Hepatology 13:422–6 (1991).

Hervé Lerat, et al., "Hepatitis C Virus Transgenic Mice as Model for HCV Associated Liver Disease", Hepatology 28 (4Pt2); 498A (1998).

Youhua Liu, et al., "Molecular Cloning and Characterization of cDNA Encoding Mouse Hepatocyte Growth Factor", Biochim et Biophys Acta 1216:299–303 (1993).

J. Nicolet, et al. Caractérisation de la Régénération Hépatique Chez la Souris Transgénique Albumine–Urokinase, Chirurgie 123(1):47–53, (Feb. 1998).

David W. Oldach, "Murine Model for Hepatitis C Virus Investigations", University of Maryland Balt Prof School (1998).

Joerg Petersen, et al., "Liver Repopulation with Xenogenic Hepatocytes in B and T Cell–deficient Mice Leads to Chronic Hepadnavirus Infection and Clonal Growth of Hepatocellular Carcinoma", Proc. Nat'l. Acad. Sci. USA 95:310–315 (1998).

Jonathan A. Rhim, et al., "Replacement of Diseased Mouse Liver by Hepatic Cell Transplantation", Science 263:1149–1152 (1994).

Jonathan A. Rhim, et al., "Complete Reconstitution of Mouse Liver with Xenogeneic Hepatocytes", Proc. Nat'l. Acad. Sci. USA 92:4942–4946 (1995).

Eric P. Sandgren, et al., "Complete Hepatic Regeneration After Somatic Deletion of an Albumin–Plasminogen Activator Transgene", Cell 66:245–256 (1990).

Mary Ann Sells, et al., "Production of Hepatitis B Virus Particles in Hep G2 Cells Transfected With Cloned Hepatitis B Virus DNA", Proc. Nat'l. Acad. Sci. USA 84:1005–1009 (1987).

Craig N. Shapiro, MD, "Occupational Risk of Infection with Hepatitis B and Hepatitis C Virus", Surgical Clinics North Amer. 75(6):1047–1056 (1995).

Camille Sureau, "In Vitro Culture Systems for Hepatitis B and Delta Viruses", Arch. Virol. 8:3–14 (1993).

Zhi–Chun Xie, et al., "Transmission of Hepatitis C Virus Infection to Tree Shrews", Virology 244:513–520 (1998).

* cited by examiner

CHIMERIC ANIMAL MODEL SUSCEPTIBLE TO HUMAN HEPATITIS C VIRUS INFECTION

FIELD OF THE INVENTION

The present invention relates generally to the field of infectious disease, particularly to models for viral pathogens.

BACKGROUND OF THE INVENTION

Despite their similar sounding names, human hepatitis B virus (HBV) and human hepatitis C virus (HCV) are completely different viruses. Both viruses are referred to as "hepatitis" viruses primarily because HBV and HCV infect and replicate in the liver. Aside from this, HBV and HCV are no more alike than are HIV and EBV, which each affect the immune system. In fact, HBV and HCV are so different that they are not even member of the same phylogenetic family. HBV is a member of the hepadnavirus family while HCV is a member of the flavivirus family.

HBV and HCV also differ in their infectivity. HCV is less infectious than an equivalent dose of HBV, as evidenced by the differences in acquisition rates in hospital personnel after needlestick injuries. HBV infections occur in 2–40% of HBV-contaminated needlestick events, while HCV infections occur in only 3–10% of HCV-contaminated needlestick events. These observations suggest that HCV is about three to four times less infectious than HBV (Shapiro *Surgical Clin North Amer.* 75(6):1047–56 (1995)).

HBV and HCV differ greatly in their requirements for replication as well as in the viral load during infection. HBV is capable of replicating in less differentiated systems (e.g., HepG2 cells, Sells et al. *Proc. Natl. Acad. Sci.* USA 84:1005 (1987)). In contrast, HCV replication may depend upon the presence of nontransformed hepatocytes (see, e.g., Ito et al. *J. Gen. Virol.* 77:1043 (1995)). The viral titers of patients infected with HCV are generally lower than those of HBV-infected patients. Patients infected with HBV have levels ranging from $10^5$ to $10^9$ particles per mL, compared to $10^2$ to $10^7$ particles per mL in HCV infections. These differences in viral titer may be due at least in part to the relative clearance rates of viral particles. In addition, the number of viral copies per cell is also very low in HCV infection (e.g., generally less than 20 copies per cell (Dhillon et al. *Histopathology* 26:297–309 (1995)). This combination of low viral titers and low number of viral copies per cell means that a significant number of human hepatocytes must be infected and producing virus for the infection to even be detected within serum.

The limited host range of human HBV and human HCV has proved problematic in the development of in vitro and in vivo models of infection. Humans and chimpanzees are the only animals susceptible to human HBV infection; human, chimpanzees, and tree shrews are susceptible for infection with human HCV (Xie et al. *Virology* 244:513–20 (1998), reporting transient infection of tree shrews with HCV). Human HBV will infect isolated human liver cells in culture (see, e.g., Sureau *Arch. Virol.* 8:3–14 (1993); Lampertico et al. *Hepatology* 13;422–6 (1991)). HCV has been reported to infect primary cultures of human hepatocytes; however, the cells do not support the production of progeny virions (Fournier et al. *J Gen Virol* 79(Pt 10):2367–74 (1998)). The development of a satisfactory in vivo model is required in order to provide a more clinically relevant means for assaying candidate therapeutic agents. The extremely narrow host range of HBV and HCV has made it very difficult to develop animal models. Current animal models of HBV and HCV either do not involve the normal course of infection, require the use of previously infected human liver cells, or both (see, e.g., U.S. Pat. Nos. 5,709,843; 5,652,373; 5,804,160; 5,849,288; 5,858,328; and 5,866,757; describing a chimeric mouse model for HBV infection by transplanting HBV-infected human liver cells under the mouse kidney capsule; WO 99/16307 and Galun et al. *J. Infect. Dis.* 172:25–30 (1995), describing transplantation of HCV-infected human hepatocytes into liver of immunodeficient mice; Bronowicki et al. *Hepatology* 28:211–8 (1998), describing intraperitoneal injection of HCV-infected hematopoietic cells into SCID mice; and Lerta et al. *Hepatology* 28(4Pt2):498A (1998), describing mice transgenic for the HCV genome). Infection by human HBV is fairly well mimicked by infection of woodchucks with woodchuck hepatitis virus (WHV) and by infection of Peking ducks with duck hepatitis virus (DHV). WHV-infected woodchucks and DHV-infected ducks have been successfully used to identify drugs effective against human HBV infection of humans. However, no analogous animal model of infection has been identified for human HCV.

In the absence of a practical non-human host, the most desirable animal model would be a chimeric animal model that allowed for infection of human liver cells through the normal route of infection, preferably a mouse model susceptible to viral infection through intravenous inoculation and that could support chronic infection. Unfortunately, the development of mice having chimeric livers with human hepatocytes susceptible to HBV or HCV infection, and sustaining viral replication and virion production at clinically relevant, sustainable levels has proven no simple matter. The field of xenogeneic liver transplantation has moved very slowly and met with many obstacles. The first advance was the development of a mouse transgenic for an albumin-urokinase-type plasminogen activator construct (Alb-uPA) (Heckel et al. *Cell* 62:447–56 (1990); Sandgren et al. *Cell* 66:245–56 (1991)). The Alb-uPA transgene includes a murine urokinase gene under the control of the albumin promoter, resulting in the targeting of urokinase production to the liver and producing a profoundly hypofibrinogenemic state and accelerated hepatocyte death. Later work with this transgenic animal demonstrated that individual hepatocytes that spontaneously deleted the transgene acquired a significant survival and replicative advantage, resulting in repopulation of the liver with these nontransgenic cells Sandgren et al., (1991), supra). The Alb-uPA transgenic mouse has proved amenable to transplantation with liver cells from non-transgenic mice (Rhim et al. *Science* 263:1149–52 (1994)). The Alb-uPA transgenic mouse was also successfully used to produce mice having chimeric livers with rat hepatocytes (Rhim et al. *Proc. Natl. Acad. Sci.* USA 92:4942–6 (1995)) or woodchuck hepatocytes (Petersen et al. *Proc. Natl. Acad. Sci.* USA 95:310–5 (1998). However, these developments were still a long step away from the development of an animal model susceptible to HBV infection or—even more challenging—susceptible to HCV infection. Production of mouse having a xenogeneic transplant from another member of the Rodentia family is not nearly as difficult or unexpected as production of a mouse having a xenogeneic transplant from an animal of a different family, e.g., a human. Hepatocyte growth factor (HGF) is the most potent stimulus of hepatocyte regeneration in vivo; in comparing sequence data, mouse HGF was shown to have 98.5% amino acid sequence homology with rat HGF, and only 90.9% with human HGF (Liu et al.

Biochim et Biophys Acta 1216;:299–303 (1993)). There were no guarantees of success.

There is a need in the field for a human-mouse liver chimera susceptible to chronic infection by HBV or with HCV and with viral production at clinically relevant levels. The present invention addresses this problem.

SUMMARY OF THE INVENTION

The present invention features a non-human animal model that is susceptible to infection by human hepatotrophic pathogens, particularly human hepatitis C virus (HCV). The model is based on a non-human, immunocompromised xenogeneic transgenic animal having a human-mouse chimeric liver, where the transgene provides for expression of a urokinase-type plasminogen activator in the liver. The invention also features methods for identifying candidate therapeutic agents, e.g., agents having antiviral activity against HCV infection.

A primary object of the invention is to provide a non-human animal model that is susceptible to infection by human HCV via the normal route of infection.

An advantage of the invention is that the animal model provides the first instance of an animal that is susceptible to infection by HCV via the normal route of infection, and further that can become chronically, consistently, and stably infected at viral titers that can be equated to viral titers in HCV-infected humans.

Still another advantage of the invention is that production of the animal model does not require obtaining or handling HBV-infected or HCV-infected cells. Thus the invention avoids the need to obtain hepatocytes from HBV- or HCV-infected human donors or to culture and infect human hepatocytes in vitro. Furthermore, the animal model does not require special maintenance or handling other than that normal associated with virally-infected, immunocompromised animals.

These and other objects, advantages, and features of the invention will become apparent to those persons skilled in the art upon reading the details of the animal model and methods of its use as more fully described below.

BRIEF DESCRIPTION OF THE DRAWINGS

FIGS. 2 and 3 represent negative (nontransplanted mouse liver; FIG. 2) and positive (human liver.

DETAILED DESCRIPTION OF PREFERRED EMBODIMENTS

Before the present invention is described, it is to be understood that this invention is not limited to particular methodology, protocols, cell lines, animal species or genera, constructs, and reagents described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a liver cell" includes a plurality of such liver cells and reference to "the non-human animal" includes reference to one or more non-human animals and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

"Chimeric" as used herein (e.g., "chimeric animal" or "chimeric liver") is meant to describe an organ or animal comprising xenogeneic tissues or cells. Of particular interest is a chimeric animal, wherein the animal is chimeric due to the presence of human hepatocytes engrafted in the animal's liver.

By "immunocompromised" is meant that the animal can not mount a complete or significant immune response against the xenogeneic tissue or cells, e.g., any immune response of the host animal is such that it is ineffective in rejection of the transplanted cells.

The term "transgene" is used herein to describe genetic material which has been or is about to be artificially inserted into the genome of a mammalian, particularly a mammalian cell of a living animal.

By "transgenic animal" is meant a non-human animal, usually a mammal, having a non-endogenous (i.e., heterologous) nucleic acid sequence present as an extrachromosomal element in a portion of its cells or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal according to methods well known in the art. A "transgene" is meant to refer to such heterologous nucleic acid, e.g., heterologous nucleic acid in the form of an expression construct (e.g., for the production of a "knock-in" transgenic animal) or a heterologous nucleic acid that upon insertion within or adjacent a target gene results in a decrease in target gene expression (e.g., for production of a "knock-out" transgenic animal).

A "knock-out" of a gene means an alteration in the sequence of the gene that results in a decrease of function of the target gene, preferably such that target gene expression is undetectable or insignificant. Transgenic knock-out animals can be comprise a heterozygous knock-out of a target gene, or a homozygous knock-out of a target gene. "Knock-outs" as used herein also include conditional knock-outs, where alteration of the target gene can occur upon, for example, exposure of the animal to a substance that promotes target gene alteration, introduction of an enzyme that promotes recombination at the target gene site (e.g., Cre in the Cre-lox system), or other method for directing the target gene alteration postnatally.

A "knock-in" of a target gene means an alteration in a host cell genome that results in altered expression (e.g., increased (including ectopic) or decreased expression) of a target gene, e.g., by introduction of an additional copy of the target gene, or by operatively inserting a regulatory sequence that provides for enhanced expression of an endogenous copy of the target gene. "Knock-in" transgenics can comprise a heterozygous knock-in of the target gene or a homozygous knock-in of a target gene. "Knock-ins" also encompass conditional knock-ins.

By "operably linked" is meant that a DNA sequence and a regulatory sequence(s) are connected in such a way as to permit gene expression when the appropriate molecules (e.g., transcriptional activator proteins) are bound to the regulatory sequence(s).

By "operatively inserted" is meant that a nucleotide sequence of interest is positioned adjacent a nucleotide sequence that directs transcription and translation of the introduced nucleotide sequence of interest.

The term "therapeutic agent" as used herein refers to any molecule, e.g., protein or small molecule, pharmaceutical compound, antibody, antisense molecule, ribozyme, and the like, useful in the treatment of a disease or condition, e.g., a liver condition, including, but not necessarily limited to infection by HBV and/or HCV. For example, therapeutic agents of the invention include molecules that inhibit, ameliorate, or relieve symptoms associated with viral infection, and in particular HBV and/or HCV.

The term "unit dosage form" as used herein refers to physically discrete units suitable as unitary dosages for subjects (e.g., animals, usually humans), each unit containing a predetermined quantity of agent(s) in an amount sufficient to produce the desired effect in association with a pharmaceutically acceptable diluent, carrier or vehicle. The specifications for the novel unit dosage forms of the present invention will depend on a variety of factors including, but not necessarily limited to, the particular agent employed and the effect to be achieved, and the pharmacodynamics associated with each compound in the host.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease.

Overview

The present invention is based on the development of a murine animal model for hepatitis C virus (HCV). The murine animal model generally involves transplantation of human hepatocytes into the liver of a transgenic mouse at an appropriate stage of the host's development, preferably shortly after birth of the host. Without being held to theory, success in the development of the model is due at least in part to the following: 1) use of a host having an immunodeficient background, thus avoiding immune destruction of introduced xenogenic (human) cells; 2) the use of a transgenic animal that contains a transgene for urokinase, which provides an ongoing potent stimulus to hepatocyte growth and cellular division; and, 3) introduction of viable human hepatocytes into the host animal at an appropriate time in the hepatocyte life cycle and at an early stage of the host animal's development to provide for long-term survival of either large numbers and/or a high percentage of human cells in the host.

To the best of the inventors' knowledge, the present invention for the first time provides a non-primate host for use as a model of HCV infection that can be infected through the normal route of infection (e.g., by intravenous inoculation). This aspect of the invention is particularly important for use in the development of anti-viral agents. Furthermore, the animal model of the invention does not require the use of pre-infected human hepatocytes, thus avoiding the handling of infected tissue isolated from human donors or infecting the human hepatocytes in vitro prior to implantation.

Accordingly the invention features a chimeric animal as described above, as well as a method of producing a chimeric animal by transplanting human hepatocytes into the liver of an immunocompromised, urokinase transgene-bearing animal. In addition the invention features methods of using the chimeric animal model described herein, including methods of identifying agents for treatment of infections by a hepatotrophic microbial pathogen.

The invention will now be described in more detail.

Host Animals

The host animal is generally a non-human, immunocompromised mammal having an increased production in the liver of urokinase-type plasminogen activator (uPA) and in which human hepatocytes can be engrafted and maintained. In one embodiment, the host animal is of the genus Rodentia, preferably a mouse. In a preferred embodiment, the host animal is an immunocompromised mouse, preferably an immunocompromised mouse transgenic for urokinase-type plasminogen activator (uPA), more preferably an immunocompromised mouse comprising a transgene that provides for liver-specific production of uPA (e.g., an Alb-uPA transgene, see, e.g., Heckel et al Cell 62:447 (1990)). Mice suitable for use in the present invention can be produced from any of a variety of background strains including, but not necessarily limited to, the strains C.B-17, C3H, BALB/c, C57131/6, AKR, BA, B10, 129, etc. The host animal may be either male or female.

Immunocompromised Background

As noted above, the host animal is preferably immunocompromised. Immunocompromised mammalian hosts suitable for implantation and having the desired immune incapacity are available. Alternatively, though less preferred, immunocompromised animals can be generated from immunocompetent animals by, for example, administration of one or more compounds (e.g., cyclosporin) and other methods well known in the art. In general, the immunocompromised host can not mount a complete immune response against the xenogeneic tissue or cells. Of particular interest are animals that are immunocompromised due to a genetic defect that results in an inability to undergo germline DNA rearrangement at the loci encoding immunoglobulins and T-cell antigen receptors. Also of interest are immunocompromised animals that have one or more genetic defects that leads to significantly decreased numbers of or no detectable functional T cells, B cells, and natural killer (NK) cells relative to normal.

Of particular interest are mice that have a homozygous mutation at the scid locus (scid/scid). The scid mutation is associated with a deficiency in DNA-dependent protein kinase catalytic subunit and prevents VDJ recombination in immunoglobulin and T-cell receptor genes. Animals homozygous for the scid mutation lack functionally recombined immunoglobulin and T-cell receptor genes and thus are deficient in both T and B cell lineages. The scid/scid mutation is available or may be bred into a number of different genetic backgrounds, e.g., CB.17, ICR (outbred), C3H, BALB/c, C57B1/6, AKR, BA, B10, 129, etc. The invention can also take advantage of animals having the beige mutation (bg), which is associated with a natural killer (NK) cell deficiency. In one embodiment, mice are produced having both the scid mutation and the bg beige mutation, resulting in an animal that does not mount an effective immune response to allogeneic or xenogeneic cells or tissues introduced to the organisms.

Other exemplary immunocompromised host that are presently available include transgenic mice genetically engineered to lack the recombinase function associated with RAG-1 and/or RAG-2 (e.g., commercially available TIM™ RAG-2 transgenic), to lack Class I and/or Class II MHC antigens (e.g., the commercially available C1D and C2D transgenic strains), or to lack expression of the Bcl-2 proto-oncogene. Other mice that may be useful as recipients are NOD scid/scid; SGB scid/scid, bh/bh; CB.17 scid/hr; NIH-3 bg/nu/xid and META nu/nu. Transgenic mice, rats and pigs are available which lack functional B cells and T cells due to a homozygous disruption in the CD3F-gene. Immunocompromised rats include HsdHan:RNU-rnu; HsdHan:RNU-rnu/+; HsdHan:NZNU-rnu; HsdHan:NZNU-rnu/+; LEW/HanHsd-rnu; LEW/HanHsd-rnu/+; WAG/HanHsd-rnu and WAG/HanHsd-rnu/+.

Transgenic Expression of Urokinase

As discussed above, the chimeric animal of the invention is also a "knock-in" transgenic for expression of urokinase-type plasminogen activator (uPA). In one embodiment, the transgene is the Alb-uPA transgene, which comprises a murine albumin enhancer/promoter, the murine uPA gene coding region, an the 3' untranslated and flanking sequences of the growth hormone gene (Heckel et al. Cell 62:447–56 (1990); Sandgren et al. Cell 66:245–56 (1991)). While the host animal may be either heterozygous or homozygous for the urokinase-type plasminogen activator transgene; homozygous animals are strongly preferred as the success rate of HCV infection with such homozygous animals is greater than that with heterozygous animals. The Alb-uPA transgene results in a lethal insult to hepatocytes that carry it, and also results in a high local (intrahepatic) concentration of urokinase, which in turn processes hepatocyte growth factor to its active form within the liver. Without being held to theory, viable allogeneic or xenogeneic cells introduced at an appropriate time in the development of an Alb-uPA transgenic animal are stimulated to replicate in this environment. The donor cells thus grow to "replace" the endogenous hepatocytes that die as a result of the lethal insult of the transgene.

Isolation of Human Hepatocytes

Human hepatocytes for transplantation into the host animals are isolated from human liver tissue by any convenient method known in the art. In general, the human hepatocytes may be fresh tissue (e.g., obtained within hours of death), or freshly frozen tissue (e.g., fresh tissue frozen and maintained at or below about 0° C.). Ideally, the cells used are recently isolated (i.e., within 2 to 4 hours) from freshly obtained human liver tissue. Human hepatocytes that are placed in a defined cryopreservation media may be stored for long periods of time (e.g., in liquid nitrogen) and thawed as required, thus permitting the development of banks of stored hepatocytes. In general, it is usually important that the isolation procedure and handling and storage protocol serve to minimize warm ischemia following cessation of blood flow to the liver (e.g., generally less than about 20 min to 40 min, preferably less than about min to about 20 min) and to minimize cold ischemia that may result from storage (e.g., generally less than about 12 hr, usually less than about 1 hr to 2 hrs). In one embodiment, the human tissue is normal, e.g., having no detectable pathogens, normal in morphology and histology, and essentially disease-free).

The liver tissue can be dissociated mechanically or enzymatically to provide a suspension of single cells, or fragments of intact human hepatic tissue may be used. In a preferred embodiment, the hepatocytes are isolated from donor tissue by routine collagenase perfusion (Ryan et al. Meth. Cell Biol. 13:29 (1976)) followed by low-speed centrifugation. Hepatocytes can then be purified by filtering through a stainless steel mesh (e.g., 100 $\mu$m), followed by density-gradient centrifugation. Alternatively, other methods for enriching for hepatocytes can be used, e.g., fluorescence activated cell sorting, panning, magnetic bead separation, elutriation within a centrifugal field, etc. The final suspension used for implantation generally comprises at least about 50–75% hepatocytes, usually at least about 80–99% hepatocytes.

Transplantation of Human Hepatocytes into Hosts

The timing of the introduction of the donor hepatocytes into the transgenic, immunocompromised host may be important to the production of a chimeric liver populated with a number of human hepatocytes sufficient to render the chimeric liver susceptible to infection by a hepatotrophic pathogen and to support replication of the pathogen. This may be particularly true where the hepatotrophic pathogen exhibits low infectivity and/or low replication rates (e.g., HCV). Where the animal is murine (e.g., a mouse), the host is ideally less than 10 days to 2 weeks in age, and optimally about 7 to 10 days old, or less than or about one week (i.e., less than or about 5 to 7 days old or younger), at the time of transplantation. Without being held to theory, the timing of transplantation indicated herein is a compromise between excess technical mortality associated with very early transplantation (i.e., due to the small size of the animals) and the time for maximal replicative stimulus (e.g., the number of cell divisions in the recipient liver that occur before transplant may influence the success and extent of engraftment of the donor human cells). Furthermore, timing of transplantation is also important since the stimulus for liver cell repopulation provided by the transgene diminishes with time, and is generally depleted after the recipient is more than about 6 weeks old (Rhim et al. (1994) *Science* 263:1149–52)60%.

The human hepatocytes can be transplanted using any suitable method known in the art. Preferably, the human hepatocytes are injected intrasplenically, e.g., into the inferior splenic pole.

Successful engraftment can be monitored by conventional methods, e.g., by examining the levels of human liver-specific proteins in the host serum, e.g., human serum albumin (HA). The chimeric host can be used for experimentation (e.g., for infection with a hepatotrophic pathogen, to screen candidate agents, etc.) when suitable. Where the animal is to be infected with a hepatotrophic agent of relative low infectivity and/or low replicative capacity, the chimeric animal can be inoculated within about four to six weeks post-transplant, generally at about six weeks post-transplant, and may be as early as three weeks post-transplant.

In general, the animal host develops human chimerism within its liver such that the percentage of liver cells that are human liver cells are from at least about 20% to 50%, generally about 40% to 60% and may be up to 90% or more.

The chimeric animal can be maintained with functional transplanted hepatocytes for at least several weeks, generally at least about 5 weeks, more usually at least about 12 weeks to 24 weeks, up to 8 months or more, and may be up to the lifespan of the host. Chimeric animals can be infected with a hepatotrophic pathogen (e.g., HBV or HCV), particularly a hepatotrophic pathogen having a host range limited to primates, particularly humans. Depending upon the nature of the pathogen, chronically infected chimeric hosts can be maintained for a period of weeks to months. For example, where the hepatotrophic pathogen is HCV, the chimeric animal can become chronically infected with HCV (e.g., chronically infected) and maintain an active HCV infection for a period of at least about 5 weeks, generally at least about 14 weeks to about 20 weeks or more, and may be for the lifespan of the host.

The viral load of the infected host can be established such that it is similar to the viral load of an infected human. For example, where the pathogen is HCV, the host animal can support infection at a level of from about $10^4$ to about $10^6$ viral particles/ml serum, generally from about $10^3$ to about $10^7$ viral particles/ml serum.

The viral load of the infected host over time is substantially consistent, chronic, and stable, e.g., the number of viral particles that can be isolated from the infected, untreated host's serum does not radically fluctuate between sampling periods, e.g., an HCV-infected host of the invention that contains a high number of HCV viral particles per mL of serum at a first sampling time is positive for HCV infection at subsequent sampling times and generally has the same or similar high level of HCV particles per mL of serum. Once stable infection is established in the host, generally within about 2 to 4 weeks post-infection. In general, the viral load of the infected host does not fluctuate radically so as to allow assessment of the effect of a candidate antiviral agent, e.g., the viral titer is chronic and consistent.

Screening Assays

The chimeric animal of the invention can be used in a variety of other screening assays. For example, any of a variety of candidate agents suspected of causing or contributing to hepatic disease, as well as the appropriate antagonists and blocking therapeutic agents, can be screened by administration to the chimeric animal and assessing the effect of these agents upon function of the engrafted human cells. Function of the engrafted human liver cells can be assessed as described above (e.g., by assessing levels of human serum albumin in the host serum).

In one embodiment of particular interest, the animal model of the invention can be used to identify candidate agents that, for example, inhibit or prevent infection by, replication of, or disease symptoms caused by a hepatotrophic pathogen (e.g., bacteria, virus, parasite, especially a hepatotrophic virus such as HBV or HCV). Although the examples provided herein generally involve the use of chimeric murine hosts with a single hepatotrophic pathogen, the invention can also be used to identify a single candidate agent or a cocktail of candidate agents having activity against infection by two or more hepatotrophic agents.

"Candidate agents" is meant to include synthetic, naturally occurring, or recombinantly produced molecules (e.g., small molecule; drugs; peptides; antibodies (including antigen-binding antibody fragments, e.g., to provide for passive immunity); endogenous factors present in eukaryotic or prokaryotic cells (e.g., polypeptides, plant extracts, and the like)); etc.). Of particular interest are screening assays for agents that have a low toxicity for human cells.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Screening of Candidate Anti-HBV or Anti-HCV Agents

In one embodiment, the animal model of the invention is used to identify agents that ameliorate symptoms caused by HBV or HCV infection and/or to more directly affect a pathogenic mechanism of the infecting virus, e.g., inhibit viral infection, decrease viral replication, or otherwise disrupt the cycle of viral propagation. In general, the candidate agent is administered to the animal model of the invention, and the effects of the candidate agent assessed relative to a control. For example, the candidate agent can be administered to an HCV-infected animal of the invention, and the viral titer of the treated animal (e.g., as measured by RT-PCR of serum samples) compared to the viral titer of the animal prior to treatment and/or to a control, untreated HCV-infected animal. In general, a detectable and significant decrease in viral titer of an infected animal following treatment with a candidate agent is indicative of antiviral activity of the agent.

The candidate agent can be administered in any manner desired and/or appropriate for delivery of the agent in order to effect a desired result. For example, the candidate agent can be administered by injection (e.g., by injection intravenously, intramuscularly, subcutaneously, or directly into the tissue in which the desired affect is to be achieved), orally, or by any other desirable means. Normally, the in vivo screen will involve a number of animals receiving varying amounts and concentrations of the candidate agent (from no agent to an amount of agent hat approaches an upper limit of the amount that can be delivered successfully to the animal), and may include delivery of the agent in different formulations and routes. The agents can be administered singly or can be combined in combinations of two or more, especially where administration of a combination of agents may result in a synergistic effect.

The activity of the candidate agent can be assessed in a variety of ways. For example, where the host animal is infected with a hepatotrophic pathogen (e.g., HBV, HCV, etc.), the effect of the agent can be assessed by examining serum samples for the presence of the pathogen (e.g., titer, as in viral titer) or markers associated with the presence of the pathogen (e.g., a pathogen-specific protein or encoding nucleic acid, etc.) Qualitative and quantitative methods for detecting and assessing the presence and severity of viral infection are well known in the art. In one embodiment, the activity of an agent against HBV infection can be assessed by examining serum samples and/or tissue sections for the presence of a viral antigen (e.g., HBV surface antigen (HBsAg), HBV core antigen (HbcAg), etc.). In another embodiment, the activity of an agent against viral infection can be assessed by examining serum samples for the presence of viral nucleic acid (e.g., HCV RNA). For example, HCV RNA can be detected using, for example, reverse transcriptase polymerase chain reaction (RT-PCR), competitive RT-PCR or branched-DNA (bDNA) assay, detection of negative-strand RNA (the replicative intermediate of HCV) by RT-PCR, or sequencing of viral RNA to detect mutation/shift in the viral genome ("quasispecies evolution") with therapy. Alternatively or in addition, the host liver may be biopsied and in situ RT-PCR hybridization performed to demonstrate directly any qualitative or quantitative alterations in the amount of viral particles within tissue sections. Alternatively or in addition, the host can be euthanized and the liver examined histologically for signs of infection and/or toxicity caused by the agent.

Identified Agents

The compounds having the desired pharmacological activity may be administered in a physiologically acceptable carrier to a host for treatment. The therapeutic agents may be administered in a variety of ways, orally, topically, parenterally e.g. subcutaneously, intraperitoneally, intravascularly, by inhalation, etc. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying Agents, salts for varying the osmotic pressure or buffers for securing an adequate pH value, and skin penetration enhancers can be used as auxiliary agents.

Vaccine Development

With some modifications, the animal model of the invention can also be used to screen candidate vaccines for their ability to prevent or ameliorate infection by a hepatotrophic pathogen. In general, a "vaccine" is an agent that, following administration, facilitates the host in mounting an immune response against the target pathogen. The humoral, cellular, or humoral/cellular immune response elicited can facilitate inhibition of infection by the pathogen against which the vaccine is developed. Of particular interest in the present invention are vaccines that elicit an immune response that inhibits infection by and/or intrahepatic replication of a hepatotrophic pathogen, e.g., a microbial, viral, or parasitic pathogen, particularly a viral pathogen, e.g., HBV and/or HCV.

In this embodiment of the invention, the immune system of the immunocompromised chimeric animal is reconstituted using, for example, stem cells of human origin to provide for a human immune system in the animal. Methods for isolating human immune cells and reconstitution of the immune system of an immunocompromised animal, e.g., a mouse with an human immune system are well known in the art (see, e.g., *Nature* 335:256–59; *Proc. Natl. Acad. Sci. USA* 93(25):14720–25). In one embodiment, the human immune cells are obtained from the same donor as the human hepatocytes used in the production of the chimeric liver. In one embodiment, the human immune cells are introduced into the host according to methods well known in the art, e.g., by intraperitoneal injection.

Screening for an effective vaccine is similar to screening methods described above. In short, the candidate vaccine is administered to the chimeric animal prior to inoculation with the hepatotrophic pathogen. The candidate vaccine is generally administered by providing a single bolus (e.g., intraperitoneal or intramuscular injection, topical administration, or oral administration), followed by one or more booster immunizations. The induction of an immune response can be assessed by examining B and T cell responses that are specific for the antigen according to methods well known in the art. The immunized animal is then challenged with the hepatotrophic pathogen; normally several immunized animals are challenged with increasing titers of the pathogen. The animals are then observed for development of infection, and the severity of infection assessed (e.g., by assessing the titer of the pathogen present, examining human hepatocyte function parameters as described above, etc.). Vaccine candidates that provide for a significant decrease in infection by the pathogen and/or a significant decrease in the severity of disease that results post-challenge are identified as viable vaccines.

Other Uses

Uses of the chimeric animal of the invention that are variations upon or in addition to those described above will be readily apparent to the ordinarily skilled artisan upon reading of the present specification. For example, the chimeric animal can be infected, preferably chronically infected, with a hepatotrophic agent, and used as a source from which the agent can be isolated. This use of the chimeric animal of the invention is particularly useful where, for example, isolation of the pathogen requires biopsy from a human subject or is difficult to obtain in useful amounts; the pathogen cannot be readily cultured in vitro; culturing of the pathogen in vitro (e.g., growth in broth culture or in cultured cells) leads to changes in the pathogen that may affects its pathogenicity and/or clinical relevance; etc. In general, the chimeric animal is inoculated with the isolated pathogen by an appropriate route (e.g., by intravenous, intramuscular, intraperitoneal, or oral administration), preferably by a route of infection that best correlates with the natural route of infection in human disease. After the pathogen establishes infection of the human hepatocytes, and after a sufficient amount of time has passed to allow replication of the pathogen, the pathogen is isolated from the infected chimeric animal by an appropriate method (e.g., isolation from a blood sample, from liver, etc.).

The chimeric animal can also be used in the course of diagnosis of liver disease in a human. For example, where the patient suffers from a liver disease of unknown origin or where diagnosis without culturing of the pathogen is not definitive, a sample suspected of containing the causative agent can be isolated from the patient (e.g., from the patient's serum or from a liver biopsy). The sample can be enriched for the suspected agent, fractionated, or otherwise processed to provide it in an administrable form, and administered to the chimeric animal. The chimeric animal can then be evaluated to assess the effect of administration of the sample upon the engrafted human hepatocytes. The effect upon the human hepatocytes can be accomplished by, for example, isolation and examination of serum samples from the chimeric animal, e.g., to assess function of the engrafted human hepatocytes, and/or to detect a pathogen in the animal's serum, e.g., to detect the presence of HCV or other microbial pathogen). The human hepatocytes can also be examined histologically to determine the effect of the patient sample.

The invention can also be adapted to provide for diagnosis and rationale therapy designed on an individualized basis. For example, human hepatocytes obtained by biopsy of a patient (e.g., percutaneous needle biopsy) can be used to produce the chimeric murine host. This chimeric murine host can then be used to evaluate the hepatotrophic pathogen infecting the patient, assess the pathogen's susceptibility to therapeutic agents, and to assess the potential toxicity of the patient's hepatocytes to such therapy. Thus the invention can be designed to facilitate tailoring of therapies most effective against an individual's specific hepatotrophic pathogen complement (e.g., against one or more infecting hepatotrophic pathogens).

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

To generate an Alb-uPA transgenic mouse tolerant to human tissue grafts, mice heterozygous for the transgene (strain TgN(AlblPlau)144Bri (The Jackson Laboratory)) were crossed with animals from a C.B-17/SCID-beige lineage (rain C.B-17/GbmsTac-scid-bgN7 (Taconic Farms), homozygous). Through a series of backcrosses, the SCID-beige trait was bred to homozygosity as confirmed by quantification of total serum IgG using a sandwich ELISA technique to detect mouse IgG according to methods well known in the art. Quantification of IgG was calculated from a standard curve prepared on each plate using a mouse IgG standard (Cappel). "Leakiness" of the SCID-beige trait was defined as >1% of normal serum IgG (Bosma et al. *Ann. Rev. Immun.* 9:323 (1991)); animals with serum IgG levels above this cutoff were euthanised. At each step, animals carrying the Alb-uPA transgene were identified by PCR analysis of genomic DNA extracted from tail biopsies, using two 18-mer primers that amplify a 151 bp product from the 3' UTR of the transgene construct (Jackson Laboratories technical support). The transgene was maintained in the heterozygous state as the homozygous trait is associated with a high perinatal mortality rate secondary to bleeding complications and liver failure (Heckel et al. *Cell* 62:447 (1990)). Animals were housed in virus/antigen-free conditions, and were cared for in accordance with the guidelines established by the Canadian Council on Animal Care (1993). All animal experiments describe Herein were performed with approval from the University of Alberta Animal Welfare Committee.

Human hepatocytes for transplantation were obtained with approval from the University of Alberta Faculty of Medicine Research Ethics Board. Segments of human liver tissue (15–20 cm$^3$) obtained at laparotomy were perfused with ice-cold Ca/Mg-free PBS containing 0.5 mM Na$_2$EDTA. Prominent perfusing vessels were cannulated and the tissue was perfused for 30 minutes with recirculating carrier solution (35 mM NaCl, 3.5 mM KCl, 2.5 mM CaCl$_2$, 50 mM HEPES, pH 7.6) containing 0.38 mg/mL Liberase CI collagenase (Boeringer-Mannheim) (Ryan et al. *Surgery* 113:48 (1993); Seglen et al. *Meth. Cell Biol.* 13:29 (1976)). Hepatocytes were filtered through 100 μm stainless steel mesh, purified by density-gradient centrifugation (Percoll, density 1.04 g/mL; Sigma) at 400 g for 5 minutes, and washed twice in ice-cold HBSS prior to suspension in Belzer-University of Wisconsin solution (DuPont) at 0° C. for short-term storage prior to transplantation. Cell counts and viability were confirmed by trypan blue exclusion prior to transplantation; final viability was routinely >80%.

Animals homozygous for the SCID trait and heterozygous for the Alb-uPA transgene were crossed, and 7 day-old progeny were transplanted with 1×10$^6$ freshly isolated viable human hepatocytes. Transplantation was accomplished by intrasplenic injection. Intrasplenically injected hepatocytes rapidly translocate to the liver via the portal venous system and engraft into the parenchyma surrounding terminal portal venules (Ponder et al. *Proc. Natl. Acad. Sci. USA* 88:1217 (1991); Gupta et al. *Transplantation* 50:472 (1990)). Since the mortality associated with intrasplenic injection is minimal, the spleen was selected as the optimal site for implantation. Accordingly, offspring (5–14 days old) were anesthetized with Halothane/O$_2$, and a small left flank incision was made. Under operating magnification, 1×10$^6$ viable hepatocytes were injected into the inferior splenic pole with a 27 g butterfly injection set (Becton-Dickinson), and a single sterile titanium clip was placed across the injection site for hemostasis. The spleen was returned to the abdomen, and the flank incision was closed in two layers.

Since the production of albumin is an exclusive property of hepatocytes (Clement et al, *Hepatology* 4:373 (1984); Gunsalas et al. *Nature Medicine* 3:48 (1997)), detection of human albumin (HA) in serum samples by selective immunoprecipitation and Western blotting was employed as an indicator of graft cell function. Recipient mice were initially sampled by jugular venous puncture at four weeks post-transplant, and at weekly intervals thereafter. Aliquots of mouse serum (20 µl) were incubated with an anti-human albumin monoclonal antibody (Clone HSA-9; Sigma), and antigen-antibody complexes were precipitated with protein G-agarose (Boehringer-Mannheim). Imnunoprecipitates were heated for 5 minutes at 98° C. in SDS buffer containing 0.2 M dithiothreitol, separated by SDS-polyacrylamide gel electrophoresis and transferred to nitrocellulose. Western blots were prepared in standard fashion (Coligan et al. *Current Protocols in Immunology* (Wiley, N.Y., 1997), vol. 2, chap. 8.10.7) using a second anti-human albumin monoclonal antibody (Clone HSA- 11; Sigma) conjugated to biotin as the primary. A streptavidin-HRP conjugate (Pierce) was employed as the secondary, and chemiluminescent reagents (Pierce) were used for signal detection.

Figure 1:
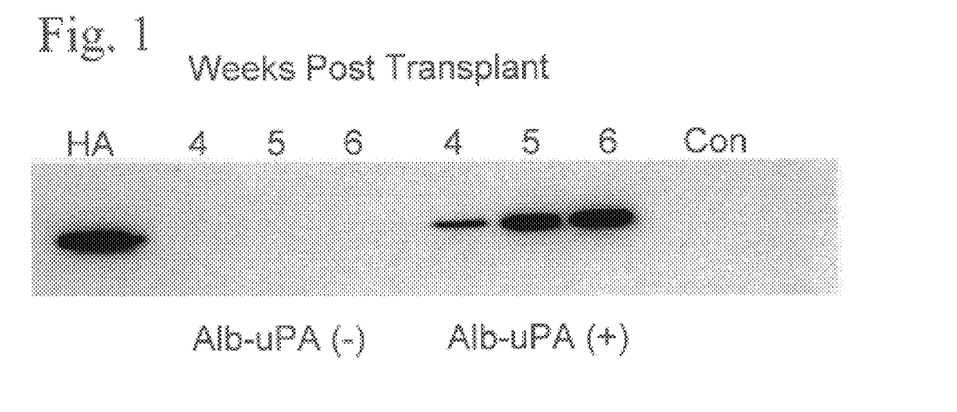
FIG. 1 is a Western blot of human albumin (HA) production in recipient serum samples over time in animals carrying or not carrying the Alb-uPA transgene
Figure 2:
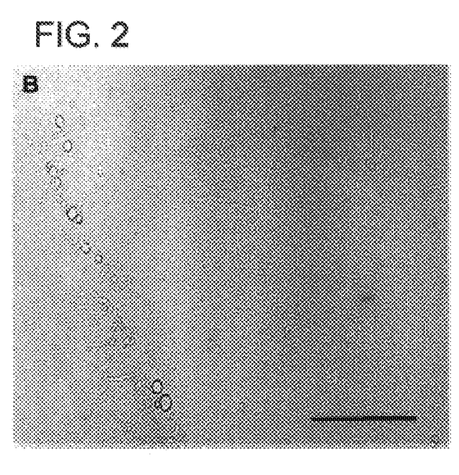
Figure 3:
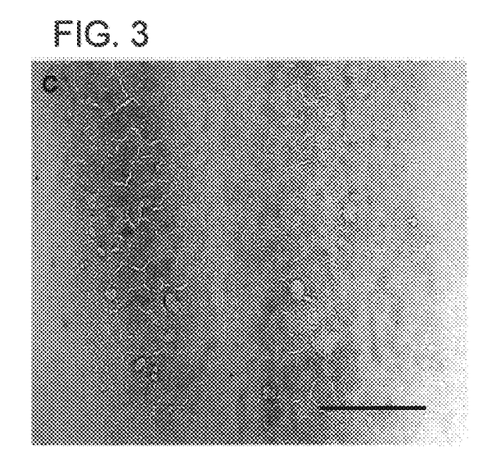
FIG. 3) controls of immunohistochemical staining of paraffin-embedded liver cryosections with an anti-human MHC Class I monoclonal antibody. Bar=250 μm

A strong HA signal was demonstrated in the serum of 4/7 transplanted littermates, indicating the presence of significant numbers of functional human hepatocytes; subsequent genotype analysis revealed that all HA-positive animals carried the Alb-uPA transgene, whereas all the animals negative for HA were also negative for the transgene. Clear HA bands were detected as early as two weeks post-transplant, with an increase in intensity over the 4–6 week timepoints, suggesting vigorous expansion of the primary cell grafts (FIG. 1). These findings indicated that the microenvironment within the Alb-uPA liver was sufficient to stimulate human hepatocytes to begin rapid proliferation, and that there was the potential to support the establishment of long-term human grafts.

To confirm proliferation and estimate the extent of replacement of murine parenchyma with human-derived cells, cryosections of recipient livers were obtained at various times after transplantation and immunostained with a monoclonal antibody specific for human MHC Class I. Segments of mouse liver were placed in OCT compound and snap-frozen in liquid nitrogen. Cryosections were fixed in acetone and embedded in paraffin; immunohistochemistry was performed as previously described (Korbutt et al. *J Clin Invest* 97:2119 (1996)). A murine monoclonal antibody specific for human MHC Class I was expressed and purified from the BB7.7 cell line (ATCC), conjugated to biotin and used as the primary antibody. An avidin/peroxidase complex (Vector; Burlingame, Calif.) was used as a secondary, with peroxide/diaminobenzidine employed as the chromagen.

Figure 4:
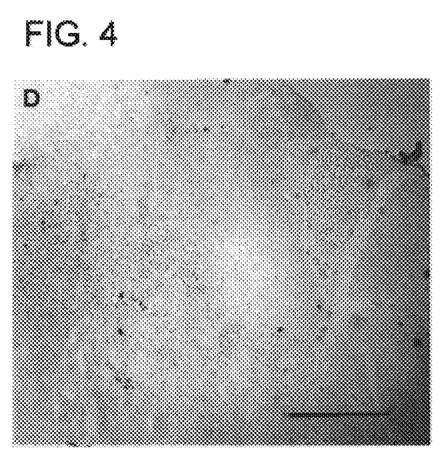
FIG. 4 illustrates a low power magnification of recipient mouse liver sectioned at four weeks post-transplant, showing engraftment of human cells with transgenic liver parenchyma. Bar=1.25 mm.
Figure 5:
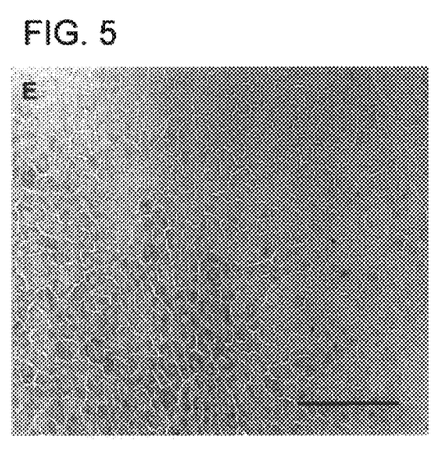
FIG. 5 provides a higher magnification of the section of FIG. 4, showing a distinct border between human and murine tissue. Bar=250 μm.

The results of these experiments are shown in FIGS. 2–5. In animals carrying the transgene, clusters of cells staining positive for human MHC (darkly stained cells) were scattered uniformly throughout the host liver at two weeks post-transplant, comprising an estimated 2–3% of all hepatocytes (FIGS. 2 (control) and 3 (transplanted)). At four weeks the percentage of positive-staining cells had increased, covering from 20 to 60% of the total surface area of individual sections (FIG. 4). The interface between human and mouse cells was distinct, with cords of human cells extending into the surrounding murine parenchyma (FIG. 5). Individual human cells maintained a normal appearance and developed sinusoidal architecture, although portal triad structures were notably absent from the regenerating nodules. This latter observation was not unexpected, since human-derived nodules are the result of clonal expansion of individual hepatocytes (Sandgren et al. *Cell* 68:245 (1991)). These nodules would contain no bile duct or endothelial precursor cells; such structures would be host-derived and therefore marginalized around proliferating human tissue.

This example demonstrates successful transplantation of the immunocompromised, Alb-uPA mice with human hepatocytes.

Example 2

To determine the long-term outcome of initial successful engraftment and proliferation, a second litter of 8 animals was transplanted in similar fashion. The hepatocytes available for use at the time of this experiment were obtained from a patient who was a chronic carrier of hepatitis B virus. The patient exhibited both a positive serum HBsAg levels and negative serum HBV DNA, indicating a chronic carrier state without active viral replication (Davis, *South. Med. J.* 90:866 (1997)).

Two randomly selected animals were sacrificed at 4 weeks for histologic analysis, and the remaining 6 animals were followed at weekly intervals. Serum samples were subjected to Western blot as described above, and the HA bands from Western blots quantified using image analysis software and band densitometry (Umax Astra 1200S scanner and VistaScan DA v.1.2.2 imaging software (UMAX Copr, Fremont, Calif.). Quantification of HA peaks was performed using NIH Image 1.60/fat software (National Institute of Health), and normalized to a 50 ng HA standard present on each blot.

Figure 6:
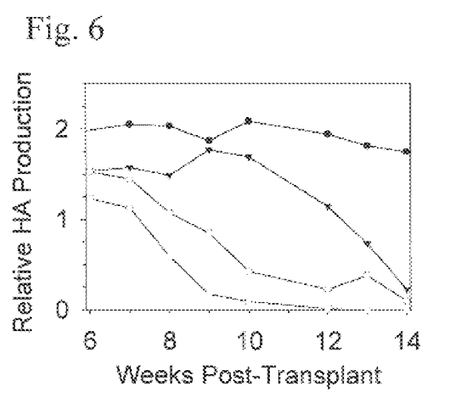
FIG. 6 is a graph illustrating production of albumin from human hepatocyte grafts ($1 \times 10^6$ cells) in four recipients carrying the Alb-uPA transgene.

Again, initial graft proliferation was seen only in the 4 animals which carried the transgene. In these animals, HA signals remained near maximal to 8 weeks at which point two distinct patterns of graft function emerged (FIG. 6; Mouse 3, open square; Mouse 4, closed triangle; Mouse 5, open circle; Mouse 6, closed circle).

Figure 7:
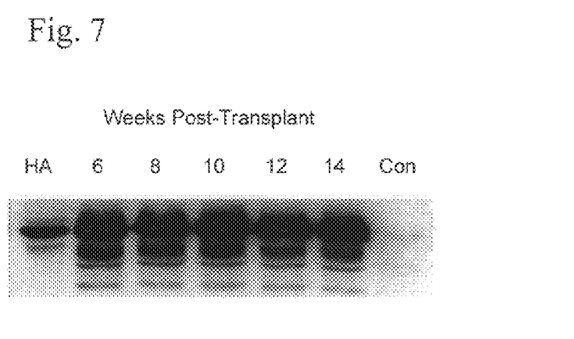
FIG. 7 is a Western blot of HA production in an Alb-uPA-positive recipient post-transplant showing sustained signal intensity. HA—human albumin standard (50 ng); Con-nontransplanted mouse serum control.

In three animals graft function began to slowly decline, with extinction of the HA signal at 10, 15 or 16 weeks. In contrast, the fourth transgenic animal (mouse no. 6) showed maximal HA production at all measured timepoints (FIGS. 6 and 7), indicating stable engraftment of human hepatocytes. Sustained graft function repeatedly occurred in approximately 25% of animals carrying the transgene. The proliferative signal for the transplanted hepatocytes is likely dependent on overall expression of the transgene, and is reduced as host-derived hepatocytes spontaneously delete the transgene.

In order to assess whether the transplanted mice supported the HBV infection of the HBV-infected, transplanted cells, serum samples from all transplanted mice were screened for hepatitis B surface antigen (HBsAg) production by sandwich ELISA. Aliquots of serum (20 µl) were tested for presence of HBsAg using a sandwich ELISA kit (Heprofile HbsAg; ADI Diagnostics) with plate analysis performed using a Dynatech MRX microplate spectrophotometer (Dynex). Both positive and negative human serum controls, as well as negative murine serum controls were included in assays.

The results are summarized in Table 1. Negative human and mouse serum controls range from 0.04–0.05 absorbance units; positive human controls range from 0.30–0.40 absorbance units.

TABLE 1

Analysis of serum markers of hepatitis B infection following transplantation of mice with HBV-infected human hepatocytes.

| Mouse | Alb-uPA Genotype | HA Expression Pattern | HBsAg Level Post-Transplant* | | | | |
|---|---|---|---|---|---|---|---|
| | | | 6 wk | 8 wk | 10 wk | 12 wk | 16 wk |
| 1 | − | Absent | ND | 0.04 | 0.04 | 0.04 | ND |
| 2 | − | Absent | 0.04 | 0.03 | ND | 0.02 | ND |
| 3 | + | Transient | 0.04 | 0.03 | 0.08 | 0.05 | ND |
| 4 | + | Transient | 0.12 | 0.04 | 0.07 | 0.04 | ND |
| 5 | + | Transient | 0.04 | 0.03 | ND | 0.04 | ND |
| 6 | + | Persistent | 0.13 | 0.13† | 3.18† | 3.78† | 3.44† |

Key: HA — human albumin; ND — not done; *HBsAg levels expressed as absorbance units.
†Samples positive for HBV DNA by PCR analysis.

As expected, control (Alb-uPA negative, nos. 1–2) mice had undetectable HBsAg levels and the three transgenic animals with transient graft function showed only sporadic minimal increases during weeks 6–12. However, the transgenic mouse with the pattern of sustained graft function (mouse no. 6) demonstrated clearly elevated levels at all time points measured, with an abrupt increase after 8 weeks to persist well within the range of HBsAg levels in actively infected human controls. The abrupt increase was suggestive of restoration of active viral replication.

To confirm active replication samples of serum taken from this animal at 8, 10, 12 and 16 weeks were analyzed by PCR for the presence of HBV DNA. DNA isolated from 12.5 µl of mouse serum were subjected to PCR using HBV-specific primers and amplification conditions previously described (Tipples et al. *Hepatology* 24:714 (1996)). All analyses were performed in blinded fashion. All four serum samples were strongly positive for the presence of viral DNA (data not shown). This result was of special interest in that despite not actively replicating within its human donor, the virus was reactivated within the immunodeficient murine host. This reactivation may have been the result of inadequate antiviral immunity, similar to what is observed in chronic HBV carriers given pharmacologic immunosuppression after organ transplantation (Terrault et al. *Gut* 40:568 (1997)).

This example thus demonstrates that human hepatocytes transplanted into chimeric, transgenic mice can support HBV viral replication.

Example 3

The success above in production of a chimeric animal that supports HBV replication in the chimeric mouse supports the use of the animal as a model of HBV. However, the vast differences between HBV and HCV discussed above (Background) meant that there could be no reasonable expectation that the animal model would be susceptible to HCV infection through a normal route of infection (e.g., intravenous transmission) or that the chimeric liver could support an active HCV infection, particularly in view of the failure of others to develop HCV animal models and the rarity of cell systems for HCV. The comparative success with HBV animals models and the repeated failures of others with HCV animal models indicate that one can not simply extrapolate from HBV to HCV. Thus, an attempt was made to establish a primary HCV infection in mice with chimeric livers using virally-infected human serum.

Seven littermates were transplanted at 7 days of age with human hepatocytes isolated from a patient serologically-negative for both HCV and HBV infection. After confirming initial graft function in 5/7 animals at 6 weeks post-transplant, all mice were inoculated intravenously with 0.25 mL of human serum obtained from an unrelated HCV-positive donor. The HCV-positive status of the human serum donor was confirmed positive for HCV RNA by PCR, with viral titers of $1 \times 10^7$ copies per ml serum. Thus, each mouse was inoculated with approximately $2.5 \times 10^6$ viral particles. Serum samples taken from all seven mice at 11, 12 and 13 weeks post-transplant (5, 6 and 7 weeks post-infection) were analyzed for the presence of HCV RNA by RT-PCR analysis using the Cobras Amplicon system (Roche Diagnostics), according to the manufacturer's instructions. Two nontransplanted mice served as mock-infected controls.

Of the five animals with good initial engraftment, four showed the pattern of transient graft function and again one animal demonstrated HA levels at maximal intensity over all measured timepoints. All three samples taken from the animal with sustained human chimerism were strongly positive for HCV RNA, and persistently positive at weekly intervals to 36 weeks. RT-PCR analysis was uniformly negative for animals negative for the Alb-uPA transgene or that only transiently expressed the HA marker for the transgene.. As 6 animals were negative for HCV RNA, the possibility of the positive RT-PCR signals in the seventh animal originating from residual virus rather than from the inoculum is remote. This example supports the conclusion that this animal had developed and at 23 weeks post-transplantation and 20-weeks post-infection, is propagating an active HCV infection at $1.2 \times 10^5 - 1.8 \times 10^5$ virion/ml serum.

This series of experiments establishes the capacity of the SCID-beige/Alb-uPA transgenic mouse to generate and sustain a chimeric human liver for prolonged and perhaps indefinite periods of time after transplantation of human hepatocytes. These chimeric organs can be infected de novo with HCV-positive human serum, and can support long-term replication (e.g., for a period of weeks or months as opposed to a few days) of human-specific hepatotrophic viruses at levels that can be equated to clinical levels in humans. HCV viral particles can be detected in serum, blood, or other blood-derived fraction by standard techniques, which techniques can be automated to facilitate more rapid screening. For example, the samples from the HCV-infection host can be diluted with known noninfected serum (e.g., about two to four fold dilution), to provide a sample volume adequate for use in an automated machine, and provide signal strengths in the assays indistinguishable from random human samples.

Long-term replication of HCV in the model of the invention (e.g., for a period longer than about 4 weeks, generally longer than about 12 weeks, e.g., about 3 months to 6 months or more) allows for the use of the model in the testing of drugs over extended periods of time, which period may be necessary for adequate drug development. For example, the effect of administration of interferon-α, an anti-HCV therapy, is generally only detectable in humans after about 12 weeks of therapy. An animal model that sustained viral replication for only a few days or weeks and/or exhibited inconsistent viral production, it would be difficult or impossible to determine if changes in viral titers were due to a candidate therapeutic or to normal fluctuations in titer inherent in the animal model. The present invention provides a model that avoids this problem.

In summary, to the best of the inventors' knowledge, this is the first report of a non-primate animal model that is susceptible to HCV infection by a normal route of infection. The model is clinically relevant (e.g., can be infected by a normal route of infection, and supports persistent HCV infection similar to that observed in humans), is cost-effective and relatively easy to produce, and will allow investigators to directly explore strategies for inhibiting viral replication in vivo.

Example 4

The above experiments of Example 3 were repeated in 18 mice. The mouse name (used as an internal reference), gender, number of copies of the Alb-uPA transgene, identify of parents and date of birth (DOB) for each animal is provided in Table 2. Mice were transplanted with either fresh (fresh) or fresh frozen (cryo) human hepatocytes at ages ranging from 7 days to 13 days. The HA signal was detected by Western blot at 5 weeks to identify those animals that were successfully engrafted. The animals were subsequently infected with HCV as described above. RT-PCR was used to detect the presence of HCV in samples form each animal as described above. The results are summarized in Table 2. Where RT-PCR was performed quantitatively to determine the number of virions per ml of serum, the data is provided. Table legend: M=male, F=female; notations under "Parents" indicates "names" of parents used as internal references; DOB=date of birth of animal; Txplt=Date of Transplant; # cells=number of cells (in millions), with f=fresh cells and c=cryopreserved cells; Txplt Age=age of animal at transplant (in days); 5 w Alb results from albumin test at 5 weeks); HCV=date of infection with HCV; RT-PCR=date of test for presence of HCV with (N)=negative and (P)=positive; and Rpt wstrn=date and results of confirmatory Western blot for presence of HCV. "Quantitative titres" indicates both the titer and the date(s) the titre was measured. Homo=homozygous for the uPA gene; Hetero=heterozygous for the uPA gene; 0=no copies of the uPA gene. Asterisks denote mice positive for HCV.

| Mouse | Sex | uPA | Parents | DOB | Txplt | # cells | Txplt Age | 5 w Alb | HCV | RT-PCR | Quantitative titres | Rpt wstrn |
|---|---|---|---|---|---|---|---|---|---|---|---|---|
| A6MRA* | M | Homo | | 30-Mar | 6-Apr | 1 M f | 7 d. | +++ | 18-May | Jun 23, 30 (P) Jul 7, 15, 21 (P) Sep 1 (P) Nov 4 (N) Jan 27 (N) Feb 26 (N) | 1.81 X 10EA - Jun 10 1.78 X 10E3 - Aug 11 1.43 X 10E3 - Aug 18 1.22 X 10E4 - Sep 21 Jul29 < 10EA Aug23 < 10E4 Oct13 < 10E3 | Feb 2 ++ |
| A27MLP | M | Hetero | | 23-Apr | 27-Apr | .5 M f | 4 d. | +++ | 15-Jun 18-Aug 3-Dec | July 7, 15, 22 (N) Aug 11(N) Sept 15, 22(N) Oct21, Nov4(N) Dec 22 (N) | | Jan 17 ++ Feb 11 ++ |
| A27MLM | M | Hetero | | 23-Apr | 27-Apr | .5 M f | 4 d. | +++ | 15-Jun 18-Aug 3-Dec | July 7, 15, 22(N) Aug11(N) Sept15, 22 (N) Oct21, Nov4(N) Dec22(N) | | Jan 17 +++ |
| A27MRA | M | Hetero | | 23-Apr | 27-Apr | .5 M f | 4 d. | +++ | 15-Jun 18-Aug 3-Dec | July7, 15, 22(N) Aug11(N) Sept15, 22(N) Oct21, Nov4(N) Dec 22 (N) | | Jan 17 - |
| Oct 12F* | F | Homo | 71F X 56M | 5-Oct | 12-Oct | 1 M f | 7 d | +++ | 3-Dec | Dec 22 (P) Jan 14 (P) Feb 11 (P) | Jan 6 1.35 X 10E6 | Feb 2 +++ |

-continued

| Mouse | Sex | uPA | Parents | DOB | Txplt | # cells | Txplt Age | 5 w Alb | HCV | RT-PCR | Quantitative titres | Rpt wstrn |
|---|---|---|---|---|---|---|---|---|---|---|---|---|
| 71Nov9FLA | F | Hetero | 71F X 56M | 30-Oct | 9-Nov | 1 M f | 10 d | +++ | 5-Jan | Jan 27 (N) | | Dec 9 +++ Feb 11 (P) +++ |
| 71Nov9FLM | F | Hetero | 71F X 56M | 30-Oct | 9-Nov | 1 M f | 10 d | +++ | 5-Jan | Jan 27 (N) | | Dec 9 +++ Feb 11 +++ |
| 71Nov9M* | M | Homo | 71F X 56M | 30-Oct | 9-Nov | 1 M f | 10 d | +++ | 5-Jan | Jan 27 (P) Feb 11 (P) | | Feb 11 +++ |
| Sep2M | M | Hetero | LP X LP | 20-Aug | 2-Sep | 1 M c | 13 d | +++ | 14-Oct | Nov 3 (N) Nov 24 (N) | | Jan 17 − |
| Sep2FRP | F | Hetero | LP X LP | 20-Aug | 2-Sep | 1 M c | 13 d | +++ | 14-Oct | Nov 3 (N) Nov 24 (N) | | Jan 17 − |
| Aug31FLM | F | 0 | LM X LM | 19-Aug | 31-Aug | 1 M f | 12 d | ++ | 14-Oct | Nov 3 (N) | | Dec 8 − |
| Nov5MRM | M | 0 | Aug 24F | 26-Oct | 5-Nov | 1 M f | 10 d | ++ | 13-Dec | Jan 6 (N) | | Feb 2 ? + |
| Nov5MLM | M | 0 | Aug 24F | 26-Oct | 5-Nov | 1 M f | 10 d | + | 13-Dec | Jan 6 (N) | | Feb 2 − |
| Aug31Msolo | M | Hetero | LA X LA | 19-Aug | 31-Aug | 1 M f | 12 d | +++ | 1-Nov | Nov 24 (N) | | Dec 8 − |
| Oct5AMRM | M | Hetero | LA X LA | 22-Sep | 5-Oct | 0.58 M f | 13 d | +++ | 3-Dec | Dec 22 (N) Jan 14 (N) | Jan 6 OD too low | Jan 7 +++ Feb 11 ++ |
| Nov16FRA* | F | Homo | LA X LA | 6-Nov | 16-Nov | 0.2 M c | 10 d | +++ | 5-Jan | Jan 27 (P) Feb 11 (P) | | Feb 11 +++ |
| Nov16FRM | F | Hetero | LA X LA | 6-Nov | 16-Nov | 0.2 M c | 10 d | ++ | 5-Jan | Jan 27 (N) | | Feb 11 − |
| Oct5BFLM | F | Hetero | 88F X 40M | 24-Sep | 5-Oct | 0.58 M f | 11 d | +++ | 3-Dec | Dec 22 (N) Jan 14 (N) | Jan 6 OD too low | Feb 11 − |
| Dec17MLM | M | Homo | 71FX56M | 13-Dec | 17-Dec | ?1M | 4 d | +++ | | 24-Feb | | |
| Nov16MLMRM | M | Hetero | LA X LA | 6-Nov | 16-Nov | 0.2 M c | 10 d | ++ | | 24-Feb | | |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A chimeric transgenic mouse host infected with human hepatitis C virus (HCV) comprising:
   an immunodeficient, transgenic mouse whose genome comprises a polynucleotide encoding a urokinase-type plasminogen activator polypeptide, wherein the polynucleotide is operably linked to a promoter such that the polypeptide is expressed in host mouse liver cells, and wherein the host is homozygous for the polynucleotide; and
   a chimeric liver comprising human hepatocytes engrafted into mouse host liver;
   wherein inoculation of the chimeric mouse host with human HCV results in HCV infection of the mouse host.

2. The chimeric mouse host of claim 1, wherein human hepatocytes constitute at least about 20% of hepatocytes in the chimeric liver.

3. The chimeric mouse host of claim 1, wherein the human hepatocytes are functional for at least about 8 weeks.

4. The chimeric mouse host of claim 1, wherein the host is infected with human hepatitis C virus following hepatocyte engraftment.

5. The chimeric mouse host of claim 4, wherein the infected host is characterized by production of at least about $10^5$ viral particles/mL of serum.

6. The chimeric mouse host of claim 4, wherein the infected host maintains consistently detectable HCV infection for a period of at least 8 weeks.

7. The chimeric mouse host of claim 1, wherein the promoter is a mouse albumin promoter.

8. The chimeric mouse host of claim 1, wherein the host immunodeficiency is caused by a scid mutation.

9. The chimeric mouse host of claim 8, wherein the host further comprises a beige mutation.

10. A method of producing a chimeric transgenic mouse host infected with human hepatitis C virus (HCV), the method comprising:
    implanting human hepatocytes into an immunodeficient, transgenic mouse host whose genome comprises a polynucleotide encoding a urokinase-type plasminogen activator polypeptide, wherein the polynucleotide is operably linked to a promoter, such that the polypeptide is expressed in host mouse liver cells and wherein the host is homozygous for the polynucleotide; and
    inoculating the host with human HCV;
    wherein a chimeric transgenic mouse host comprising a human-mouse chimeric liver and having a human HCV infection is produced.

11. A chimeric mouse host produced by the method of claim 10.

12. A method for screening candidate agents for activity against a hepatotrophic pathogen, the method comprising the steps of:
    administering a candidate agent to the chimeric mouse host of claim 1; and
    analyzing the effect of the candidate agent upon HCV infection;
    wherein a decrease in infectious load of the human HCV relative to an untreated chimeric transgenic mouse host or relative to infectious load in the chimeric transgenic mouse host prior to candidate agent administration is indicative of anti-HCV activity of the agent.

13. The method of claim 12, wherein the candidate agent is administered prior to infection with human HCV.

14. A method of culturing human hepatitis C virus (HCV), the method comprising:
   administering human HCV to the chimeric transgenic mouse host of claim 1; and
   isolating human HCV from the infected host following human HCV replication in the host.

15. The chimeric transgenic mouse of claim 1, wherein the promoter is an albumin promoter.

16. The chimeric mouse of claim 1, wherein the human hepatocytes do not contain detectable HCV prior to engraftment in the mouse liver.

17. A chimeric transgenic mouse infected with human hepatitis C virus (HCV) comprising:
   an immunodeficient mouse whose genome comprises a polynucleotide encoding a urokinase-type plasminogen activator polypeptide, wherein the polynucleotide is operably linked to a promoter such that the polypeptide is expressed in mouse liver cells and wherein the host is homozygous for the transgene; and
   a chimeric liver comprising human hepatocytes engrafted into mouse liver;
   wherein inoculation of the chimeric mouse with human HCV results in HCV infection of the mouse such that the infected mouse is characterized by production of at least about $10^4$ viral copies/mL of serum.

18. The chimeric transgenic mouse of claim 17, wherein the infected mouse is characterized by production of at least about $10^5$ viral copies/mL of serum.

* * * * *